United States Patent [19]

Kuhlmann

[11] Patent Number: 4,649,165

[45] Date of Patent: Mar. 10, 1987

[54] DENTAL FILLING MATERIAL COMPRISING POLYMERIZABLE (METH)ACRYLIC COMPOUND, X-RAY OPAQUE FILLERS AND MICROFILLER

[75] Inventor: Werner Kuhlmann, Mainz-Hechtscheim, Fed. Rep. of Germany

[73] Assignee: Blendax-Werke R. Schneider GmbH & Co., Mainz, Fed. Rep. of Germany

[21] Appl. No.: 782,713

[22] PCT Filed: Jan. 26, 1985

[86] PCT No.: PCT/EP85/00024

§ 371 Date: Sep. 27, 1985

§ 102(e) Date: Sep. 27, 1985

[87] PCT Pub. No.: WO85/03220

PCT Pub. Date: Aug. 1, 1985

[30] Foreign Application Priority Data

Jan. 30, 1984 [DE] Fed. Rep. of Germany ....... 3403040

[51] Int. Cl.$^4$ ............................................. A61K 6/06
[52] U.S. Cl. ....................................... 523/116; 523/117
[58] Field of Search ............... 523/116, 117, 109, 115

[56] References Cited

U.S. PATENT DOCUMENTS

| | | | |
|---|---|---|---|
| 4,297,266 | 10/1981 | Ibsen et al. | 523/116 |
| 4,388,069 | 6/1983 | Orlowski | 523/117 |
| 4,389,497 | 6/1983 | Schmitt et al. | 523/116 |
| 4,394,465 | 7/1983 | Podszun et al. | 523/116 |
| 4,407,984 | 10/1983 | Ratcliffe et al. | 523/116 |
| 4,427,799 | 1/1984 | Orlowski et al. | 523/116 |
| 4,544,359 | 10/1985 | Waknine | 523/116 |

*Primary Examiner*—Harold D. Anderson

[57] ABSTRACT

Dental filling material on the basis of polymerizable compounds and an inorganic filler mixture with improved properties, particularly excellent X-ray opacity and polishability, where the filler mixture essentially consists of an X-ray opaque filler with a particle size distribution of between 0,5 and 40 μm, an X-ray opaque filler with a particle size distribution of between 0,2 and 15 μm and a microfiller, particularly colloidal silica, with a particle size distribution of between 5 and 150 nm.

9 Claims, No Drawings

DENTAL FILLING MATERIAL COMPRISING POLYMERIZABLE (METH)ACRYLIC COMPOUND, X-RAY OPAQUE FILLERS AND MICROFILLER

The present invention relates to a new dental filling material containing a selected filler mixture.

Dental restoration materials on the basis of polymerizable compounds, so-called "composites", contain in addition to one or more polymerizable monomers, activators, polymerization catalysts, and other components compulsorily a mineral filler.

This filler determines according to type and amount the physical properties of the filling prepared by the composite. The higher the percentage of filler and its particle size, the better are the physical properties, but the worse is usually the polishability.

For this reason, it has been tried to improve the polishability of such materials by using fillers with smaller particle size of between approx. 10 and 300 nm; but this has diminished the mechanical properties.

These so-called "microfillers" are in particular mainly or almost exclusively used in the preparation of light-curing composites, i.e. dental restoration materials, which are present in one phase and which contain fillers, polymerizable compounds and a polymerization initiator which forms radicals under the influence of light.

This is particularly based on the fact that these materials must have a certain curing depth, which is not reached with most of the fillers with higher particle sizes, so-called "macrofillers".

Other macrofillers, which do not show this disadvantage cause discolorations during polymerization (=curing) of the filling. This applies particularly to different types of glass, which—when they are used by themselves—result in a greenish or greyish discoloration during curing of the filling and moreover are not polishable.

Moreover, also X-ray opacity of cured dental fillings is desirable, which cannot be achieved with microfillers on the basis of silica.

Therefore, there was a need to develop dental filling materials which do not show these disadvantages, which are well light-curable, if necessary even without polymerization catalysts, show no discoloration, but have good physical properties, particularly reduced water absorption and shrinkage, a coefficient of thermal expansion tending to zero and improved mechanical properties, particularly regarding hardness and diametrical tensile strength, and being also X-ray opaque.

Moreover, it is desirable to reach a polishability which is at least satisfactory.

According to the invention, it has been found now that a dental filling material having the described properties may be prepared by using as inorganic filling material in an amount of approx. 60 to approx. 90% by weight of the total composition a mixture of (a) at least one optionally silanized X-ray opaque inorganic filler with a particle size distribution of between 0,5 and 40 μm in an amount of approx. 5 to approx. 20, particularly approx. 10 to approx. 15% by weight of the filler mixture, (b) at least one optionally silanized X-ray opaque inorganic filler with a particle size distribution of between 0,2 and 15 μm in an amount of approx. 20 to approx. 40, particularly approx. 25 to approx. 35% by weight of the filler mixture, and (c) an optionally silanized inorganic microfiller, particularly silica, with a particle size distribution from 5 to 150 nm in an amount of approx. 40 to approx. 75, particularly approx. 55 to approx. 65% by weight of the filler mixture.

The precise particle size distribution of the X-ray opaque filler with a higher medium particle diameter contained in an amount of 5 to 20, preferably 10 to 15, particularly approx. 10% by weight of the total filler usually is as following:

| 5%  | 0,5–1 μm  |
|-----|-----------|
| 10% | 1–2 μm    |
| 20% | 2–5 μm    |
| 20% | 5–10 μm   |
| 30% | 10–20 μm  |
| 15% | 20–40 μm  |

The exact particle size distribution of the X-ray opaque filler with a smaller medium particle diameter contained in an amount of 20 to 40, preferably 25 to 35, particularly approx. 30% by weight of the total filler is shown in the following table:

| 5%  | 0,2–0,5 μm |
|-----|------------|
| 10% | 0,5–1 μm   |
| 15% | 1–2 μm     |
| 45% | 2–5 μm     |
| 20% | 5–10 μm    |
| 5%  | 10–15 μm   |

The particle size of the microfiller contained in an amount of 45 to 75, preferably 55 to 65, particularly approx. 60% by weight, calculated in relation to the total filler, is between approx. 5 to approx. 150, preferably approx. 120 nm; the preferred medium particle size is between approx. 30 and approx. 60, preferably approx. 40 nm.

The X-ray opaque components (a) and (b) with different particle sizes may be of identical or different chemical structure.

In order to improve the incorporation of the filler mixture according to the invention into the composition and the compatibility with the organic compounds, it is suitable to silanize these fillers with an organosilane. The silanization may be effected with any suitable organosilane of the general formula:

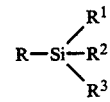

where R, $R^1$, $R^2$ and $R^3$ represent the same or different organic groups, provided that at least 1 group means an OH-group, or a group which can be transferred into an OH-group, e.g. by hydrolysis, particularly an alkoxy group. Preferred organosilanes are (meth)acroyl propyl dihydroxymethoxysilane, (meth)acroyl propyl hydroxydimethoxysilane, (meth)acroyl propyl trimethoxysilane or its mixtures; however, also vinyl triethoxysilane or vinyl tri(methoxyethoxy)silane are expecially suitable silanization agents.

Suitable inorganic X-ray opaque fillers are particularly the different barium silicate glasses, e.g. of the empirical composition 66 (mol.-%) $SiO_2$, 17 BaO, 11 $B_2O_3$ and 6 $Al_2O_3$, lithium aluminum silicate, glass ceramics fillers, etc., such X-ray opaque fillers are e.g. described in U.S. Pat. Nos. 3, 801, 344, 3,808,170 and 3,975,203 as well as in German Offenlegungsschrift No. 2, 347, 591.

A preferred microfiller is precipitated or pyrogenic silica, e.g. of the type "Aerosil", particularly silanized.

Such a suitable material is described in German Offenlegungsschrift No. 2, 403, 211 and particularly in European Patent Application No. 60, 911.

As already explained, the dental filling materials according to the invention are particularly suitable for the use in light-curing products, i.e. products which are present in one phase and polymerize under the influence of light.

Such compositions contain one or more photopolymerization initiators. Particularly suitable photopolymerization initiators are carbonyl compounds such as benzoin and its derivatives, particularly benzoin methyl ether, benzil and benzil derivatives, e.g. 4,4-oxydibenzil or other dicarbonyl compounds, e.g. diacetyl, 2,3-pentanedione or metal carbonyls, quinone, particularly campheroquinone or its derivatives. The percentages of photopolymerization initiator amounts from approx. 0,01 to approx. 5% by weight of the total composition.

These light-curable, i.e., photopolymerizable preparations preferably contain also so-called polymerization accelerators. These are substances which accelerate the polymerization reaction when polymerization initiators are present. Known accelerators are e.g. amines, such as p-toluidine, N,N-dimethyl-p-toluidine, N,N-di(hydroxyethyl)-p-toluidine, trialkyl amines such as trihexyl amine, polyamines such as N,N,N',N'-tetraalkyl alkylene diamines, barbituric acid and dialkyl barbituric acid and sulfimides, preferably in an amount of approx. 0,01 to approx. 5% by weight of the total composition.

Suitable accelerators are e.g. described by G. M. Brauer et al., Journal of Dental Research, Vol. 58/No. 10 (1979), p. 1994–2000.

A preferred light-curable dental filling material contains approx. 60 to approx. 90% by weight of the total composition of an inorganic filler mixture of the type described above.

The preferred particle size distribution of the total filler mixture is shown in the following table:

| ~60% | 0,005–120 nm | (pyrogenic SiO$_2$, average primary particle size ~40 nm) |
|---|---|---|
| ~1,5% | 0,2–0,5 μm | |
| ~3,5% | 0,5–1 μm | |
| ~5 | 1–2 μm | |
| ~16% | 2–5 μm | |
| ~8% | 5–10 μm | |
| ~5% | 10–20 μm | |
| ~1% | 20–40 μm | |

Of course, it is also possible to use the dental filling materials according to the invention as two-phase preparations, where one phase contains a polymerization catalyst, e.g. a peroxide, and the other phase contains an accelerator for this peroxide, e.g. an organic amine, and where the two phases are brought together immediately before the illing of the tooth and the polymerization take place in the drilled cavity to be filled, which is preferably provided with a reliner or a bonding agent.

Suitable peroxides which decompose under formation of radicals when polymerization is initiated are e.g. aryl peroxides such as benzoyl peroxide, cumene peroxide, urea peroxide, tert.-butyl hydroperoxide or -perbenzoate and silyl peroxides, preferably in amounts of approx. 0,01 to approx. 5, particularly approx. 0,5 to 2,5% by weight of the total composition.

If the one phase of the two-phase agent contains a polymerization initiator, an accelerator of the above described type, preferably an amine or barbituric acid or its derivatives, e.g. a dialkyl barbituric acid, is added to the other phase.

In principle, all compounds which are proposed and suitable for this purpose can be used as polymerizable monomers in the dental filling materials according to the invention. Particularly mentioned are the known reaction products from Bisphenols, particularly Bisphenol A, and glycidyl methacrylate, known under the abbreviation Bis-GMA, the various alkanediol dimethacrylates such as 1,6-hexanediol methacrylate, 1,4-butanediol dimethacrylate, tri- or tetraethyleneglycol dimethacrylate, bis-(2-methacroylpropyl)-phthalate, -isophthalate or -terephthalate, trimethylolpropanedi- and -trimethacrylate, as well as particularly the reaction products from diisocyanates and hydroxyalkyl methacrylates, as e.g. described in German Offenlegungsschrift No. 2, 312, 559, adducts from (di)isocyanates and 2,2-propane-bis-[3-(4-phenoxy)-1,2-hydroxypropane]-1-methacrylate according to U.S. Pat. No. 3, 629, 187 as well as particularly the adducts from isocyanates and methacroyl alkyl ethers, -alkoxy benzenes and/or -alkoxycycloalkanes, as described in European Pat. No. 44, 352.

Of course, also mixtures of suitable monomers are used.

It is suitable to add to dental filling materials, UV-stabilizers to avoid discoloration of the cased fillings during aging. A particularly suitable UV-stabilizer is 2-hydroxy-4-methoxy benzophenone. Another preferred material is 2-(2'-hydroxy-5'-methylphenyl)benzotriazol; however, in principle every physiologically inert UV-absorbing agent is suitable for this purpose, e.g. hydroquinone, p-benzoquinone, p-butyl hydroxy toluene and others. The latter compound can also act as an antioxidant in the filling.

A survey on the substances normally used in dental filling materials can be found in the Article of R. L. Bowen in Journal of Dental Research, Vol. 58/5 (May 1979), p. 1493–1503 as well as in the subsequent supplement of J. F. Lann, p. 1504–1506.

In order to achieve an impression as close as possible to nature of the filled tooth surfaces, composite materials contain, if necessary, a low percentage of dyestuffs or pigments.

The following examples illustrate the invention:

EXAMPLE 1

| | |
|---|---|
| Pyrogenic silica of the type "Aerosil$^R$" (mean particle size ~40 nm) | 42,0 (parts by weight) |
| Barium borealuminum silicate glass (particle size ~0,2–15 μm) | 21,0 |
| Barium aluminum silicate glass (particle size ~0,5–40 μm) | 7,0 |
| Methacroyl propyl trihydroxysilane (calculated to the fillers) | 3,0 |
| Reaction product from glycidyl methacrylate and Bisphenol A (Bis-GMA) | 15,5 |
| Triethyleneglycol dimethacrylate | 10,5 |
| Campheroquinone | 0,15 |
| Ethyl benzoin | 0,15 |
| Dimetnyl aminoethyl methacrylate | 0,4 |

-continued

| | |
|---|---|
| Hydroquinone monomethylether, UV-stabilizer, dyestuffs | q.s. |

After light-curing an X-ray opaque polishable filling was obtained.

EXAMPLE 2

| | Part A | Part B |
|---|---|---|
| Pyrogenic silica (mean particle size ~50 nm | 40 | 40 (parts by weight) |
| Barium aluminum silicate glass (particle size 0,2–15 μm) | 22 | 22 |
| Barium aluminum silicate glass (particle size 0,5–40 μm) | 6,5 | 6,5 |
| Methacroyl propyl trihydroxysilane (calculated to the fillers) | 3,2 | 3,2 |
| Bis-GMA | 15,8 | 15,8 |
| 1,6-hexanediol dimethacrylate | 10,5 | 10,6 |
| Benzoyl peroxide | — | 0,4 |
| N,N—diethanolo-p-toluidine | 0,5 | — |
| UV-absorber, stabilizers, dyestuffs | q.s. | q.s. |

After having mixed together both parts, a polishable, X-ray opaque polymerizate with excellent physical properties was obtained.

EXAMPLE 3

| | |
|---|---|
| Colloidal silica (mean particle size ~60 nm, organosilicone contents ~8%) | 44,5 (parts by weight) |
| Barium aluminum silicate glass (silanized; particle size 0,2–15 μm) | 22,3 |
| Lanthane glass (silanized; particle size 1–30 μm) | 7,6 |
| Bis-GMA | 10,0 |
| 1,6-hexanediol dimethacrylate | 8,5 |
| Trimethylolpropane trimethacrylate | 5,8 |
| Diethyl aminoethyl methacrylate | 0,4 |
| Benzil | 0,4 |
| UV-absorber. stablizer, dyestuffs | q.s. |

After light-curing a color-stable, X-ray opaque, polishable material with good mechanical properties was obtained.

What is claimed is:

1. Dental filling material comprising (i) one or more polymerizable (meth) acrylic compounds, (ii) polymerization accelerators, polymerization initiators or mixtures thereof and about 60 to 90% by weight, based on the total composition, of an inorganic filler mixture of at least two X-ray opaque fillers with different particle size distribution which comprises:
   (a) about 5 to 20% by weight, based on the total filler mixture, of at least one X-ray opaque filler with a particle size distribution of between 0.5 to 40 micrometers,
   (b) about 20 to 40% by weight, based on the total filler mixture, of at least one X-ray opaque filler with a particle size distribution of between 0.2 and 15 micrometers, and
   (c) about 40 to 75% by weight, based on the total filler mixture, of at least one microfiller with a particle size distribution between 5 and 150 nanometers.

2. Dental filling material according to claim 1 containing about 10 to 15% by weight, based on the total filler mixture, of filler (a).

3. Dental filling material according to claim 1 containing about 25 to 35% by weight, based on the total filler mixture, of filler (b).

4. Dental filling material according to claim 1 containing about 55 to 65% by weight, based on the total filler mixture, of microfiller (c).

5. Dental filling material according to claim 1 wherein the microfiller is colloidal silica.

6. Dental filling material according to claim 1 wherein the microfiller (c) has an average particle size of about 30 to 60 nanometers.

7. Dental filling material according to claim 1 wherein filler (a) has the following particle size distribution:

| | |
|---|---|
| about 5% | 0.5–1 micrometers, |
| about 10% | 1–2 micrometers, |
| about 20% | 2–5 micrometers, |
| about 20% | 5–10 micrometers, |
| about 30% | 10–20 micrometers, |
| about 15% | 20–40 micrometers, |

8. Dental filling material according to claim 1 wherein filler (b) has the following particle size distribution:

| | |
|---|---|
| about 5% | 0.2–0.5 micrometers, |
| about 10% | 0.5–1 micrometers, |
| about 15% | 1–2 micrometers, |
| about 45% | 2–5 micrometers, |
| about 20% | 5–10 micrometers, |
| about 5% | 10–15 micrometers. |

9. Dental filling material according to claim 1 wherein at least one of filler (a), filler (b) and microfiller (c) is silanized.

* * * * *